United States Patent [19]
Sørensen et al.

[11] Patent Number: 5,899,212
[45] Date of Patent: May 4, 1999

[54] RE-FORMATION OF KERATINOUS FIBRE CROSS LINKS

[75] Inventors: Niels Henrik Sørensen, Skævinge, Denmark; Jason Patrick McDevitt, Wake Forest, N.C.

[73] Assignee: Novo Nordisk A/S, Novo Alle, Denmark

[21] Appl. No.: 09/074,427

[22] Filed: May 7, 1998

[51] Int. Cl.[6] .................................................. A45D 7/04
[52] U.S. Cl. .......................... 132/203; 132/200; 132/208; 8/401; 435/189
[58] Field of Search ................................. 132/203, 202, 132/204, 207, 208, 209, 210, 200; 8/401, 410, 416, 421, 424, 429, 406, 267; 435/189, 267

[56] References Cited

U.S. PATENT DOCUMENTS

| | | | |
|---|---|---|---|
| 2,539,202 | 1/1951 | Peek | 435/189 |
| 3,200,040 | 8/1965 | Lange | 8/401 |
| 3,210,252 | 10/1965 | Blanke et al. | 8/401 |
| 3,251,742 | 5/1966 | Soloway | 8/401 |
| 3,957,424 | 5/1976 | Zeffren et al. | 8/401 |

FOREIGN PATENT DOCUMENTS

| | | | |
|---|---|---|---|
| 0 328 816 | 8/1989 | European Pat. Off. | |
| 504005 | 9/1992 | European Pat. Off. | 132/203 |
| WO 97/19998 | 6/1997 | WIPO | |
| WO 97/19999 | 6/1997 | WIPO | 132/203 |

OTHER PUBLICATIONS

Toshio Isaji, Abstract of GB 1077758 (Aug. 2, 1967).

*Primary Examiner*—Gene Mancene
*Assistant Examiner*—Pedro Philogene
*Attorney, Agent, or Firm*—Steve T. Zelson; Elias J Lambiris; Carol E. Rozek

[57] ABSTRACT

The present invention relates to a method for re-forming keratinous fibre cross links comprising contacting at least one oxidoreductase with the keratinous fibres for a sufficient period of time and under conditions sufficient to permit re-formation of keratinous fibre cross links. The method may be performed simultaneously with dyeing of said keratinous fibres. The invention also relates to the use at least one oxidoreductase for re-formation of keratinous fibre cross links.

19 Claims, No Drawings

RE-FORMATION OF KERATINOUS FIBRE CROSS LINKS

FIELD OF THE INVENTION

The present invention relates to a method for re-forming keratinous fibre cross links of hair and other fibres by means of at least one oxidoreductase, to a method for re-forming keratinous fibre cross links and simultaneously dyeing of keratinous fibres by means of at least one oxidoreductase, to the use of oxidoreductases for re-formation of keratinous fibre cross links and to the use of oxidoreductases for re-formation of the keratinous fibre cross links of hair and simultaneously dyeing said hair.

BACKGROUND OF THE INVENTION

Hair setting processes, including both permanent and straightening, are usually carried out at room temperature. The process typically includes two phases, namely i) reducing covalent disulfide linkages in the keratinous fibres of the hair, thereby rendering the hair deformable without elasticity, the hair typically being wetted by a solution containing a reducing agent and afterwards rolled on curlers (or mechanically straightened), and ii) re-establishment of a network of cross links in the keratinous fibres of the hair by application of a so-called fixer (which usually contains an oxidising agent), thereby rendering the curly or straightened shape "permanent".

For the purpose of breaking the disulfide cross linkages a number of organic reducing agents can be used, including strong bases such as sodium hydroxide. Thioglycolic acid, thioacetic acid and other sulphur-containing compounds are also commonly used.

Among reagents used for the purpose of fixation of the hair, i.e., compounds capable of re-establishing the physico-mechanical properties of the hair by forming disulfide and other cross links between keratin chains, hydrogen peroxide is the most commonly used reagent as hydrogen peroxide reacts rapidly with the keratin —SH groups. Other examples of commonly used oxidising agents are e.g. perborates, bromates, chlorites, iodates, bromates, persulphates and tetrathionates.

In principle, it is possible to use atmospheric oxygen as an oxidising agent. The direct use of atmospheric oxygen, however, suffers from the disadvantage that several hours are required in order to complete the reaction.

The use of hydrogen peroxide (and other oxidising agents) is preferably avoided as e.g. hydrogen peroxide is known to be caustic to the skin and, accordingly, causes an unsatisfactory working environment for e.g. hair dressers. Furthermore, hydrogen peroxide can damage hair.

Thus, there is a need for a method which may replace the use of hydrogen peroxide and other hazardous oxidising agents in re-formation of keratinous fibre cross links. The method should preferably avoid the use of hazardous chemicals and, at the same time, be easily conducted within a reasonable time, ideally within the time normally required for hydrogen peroxide treatment. Traditionally, hair setting (i.e., waving and straightening) and hair dyeing have been considered as two independent processes, each process being carried out individually by means of different techniques.

Permanent hair dyes are durable to sunlight, shampooing and other hair treatments and need only to be refreshed once a month as new hair grows out. With these dyeing systems the dyes are created directly in and on the hair. Small aromatic colourless dye precursors (e.g., p-phenylenediamine and o-aminophenol) penetrate deep into the hair where the precursors are oxidised by an oxidising agent into coloured polymeric compounds. These coloured compounds are larger than the dye precursors and cannot be washed out of the hair.

Traditionally, $H_2O_2$ is used as the oxidising agent, but also as a bleaching agent. Thus, dyeing compositions comprising $H_2O_2$ are often referred to as "lightening dyes" due to this lightening effect of $H_2O_2$.

The use of $H_2O_2$ in dye compositions has some disadvantages as $H_2O_2$ damages the hair. Further, oxidative dyeing often requires high pH (normally around pH 9–10), which also inflicts damage on the hair. Consequently, if using dye compositions comprising $H_2O_2$, it is not recommendable to dye the hair often.

To overcome the disadvantages of using $H_2O_2$ it has been suggested to use oxidation enzymes to replace $H_2O_2$.

U.S. Pat. No. 3,251,742 (Revlon) describes a method for dyeing human hair by dye formation in situ (i.e., on the hair). An oxidative enzyme is used for the colour formation reactions at a substantially neutral pH (pH 7–8.5). Laccases, tyrosinases, polyphenolases and catacolases are mentioned as suitable oxidation enzymes.

EP patent No. 504.005 (Perma S.A.) concerns compositions for hair dyeing which do not require the presence of $H_2O_2$ (hydrogen peroxide). The compositions comprise an enzyme capable of catalysing the formation of the polymeric dyes and also dye precursors, such as bases and couplers, in a buffer solution wherein the pH of the composition is between 6.5 and 8 and the enzyme has an optimal activity in the same pH range.

A method for enzyme-mediated dyeing of keratinous fibres, such as hair, has been described in WO 97/19999 (Novo Nordisk) and WO 97/19998 (Novo Nordisk).

Canadian patent 67:93913 discloses a composition containing a metal-containing dye for simultaneously permanent waving and dyeing hair. EP patent No. 328816 describes a process for dyeing of waved or relaxed hair using a metal ion-catalyzed hair dyeing composition.

Until now, there has been not a commercially acceptable method for simultaneously performing permanent dyeing and setting of hair. This is because hair that has been reduced as part of a setting treatment (waving or straightening) will be badly damaged by exposure to hydrogen peroxide at concentrations that are used in conventional permanent hair dyeing products.

A commercially relevant method that would allow simultaneous permanent dyeing and setting of hair would be desired by hairdressers and consumers alike. It will give consumers an entirely new wave of options in their hair style choices. It will also increase convenience and efficiency, in addition to decreasing safety hazards, for both hairdressers and consumers.

Accordingly, there is a need for a method which can be used for simultaneous permanent setting and dyeing of keratinous fibres such as hair.

The method of the present invention overcomes this limitation by providing a mild, peroxide-free method of dyeing hair and re-forming cross links in hair after a reducing treatment. As a result, this method allows simultaneous permanent setting and dyeing of hair without causing excessive damage to the hair.

SUMMARY OF THE INVENTION

In one aspect, the present invention relates to a method for re-forming keratinous fibre cross links comprising contacting at least one oxidoreductase with keratinous fibres for a sufficient period of time and under conditions sufficient to permit re-formation of keratin fibre cross links of especially hair.

Further, the invention also provides the possibility of setting and dyeing keratinous fibres simultaneously (i.e., in a one-step process). The method of the present invention provides a mild, peroxide-free method of dyeing hair and re-forming cross links in hair after a reducing treatment.

In the context of the present invention the term "re-formation of cross links" is not intended to exclusively encompass restoration of the original disulfide cross links of keratinous fibres, but rather includes formation of any disulfide cross links, as well as covalent cross links resulting from thioethers ("lanthionines"), amines, ethers, and other covalent bonds, in addition to ionic bonds and hydrogen bonds.

Further, the purpose for re-forming cross links by "setting" includes waving and straightening of the keratinous fibres, in particular hair.

When mentioning "keratinous fibres" in connection with the present invention, it is intended to cover all sorts of keratinous fibres, such as human or animal hair, fur, hide, wool and the like.

In another aspect, the invention relates to the use of at least one oxidoreductase for re-formation of keratinous fibre cross links.

The present invention also relates to a method for re-forming keratinous fibre cross links and simultaneously dyeing keratinous fibres comprising contacting at least one oxidoreductase and at least one precursor with the keratinous fibre for a sufficient period of time and under conditions sufficient to permit oxidation of the precursor into a coloured compound (i.e., a dye) and to permit re-formation of keratinous fibre cross links.

In a further aspect, the invention relates to the use of at least one oxidoreductase in combination with at least one precursor for re-formation of keratinous fibre cross links and simultaneously dyeing said keratinous fibres.

DETAILED DESCRIPTION OF THE INVENTION

It is the object of the present invention to provide a method for re-forming cross links of keratinous fibres such as hair comprising contacting at least one oxidoreductase with the keratinous fibres for a sufficient period of time and under conditions sufficient to permit re-formation of keratinous fibre cross links.

The present invention also relates to a method for re-forming keratinous fibre cross links and simultaneously dyeing keratinous fibres comprising contacting at least one oxidoreductase and at least one precursor with the keratinous fibres for a sufficient period of time and under conditions sufficient to permit oxidation of the precursor into a coloured compound and to permit re-formation of keratinous fibre cross links.

Oxidoreductases

Oxidoreductases (i.e., enzymes classified under the Enzyme Classification number E.C. 1 (Oxidoreductases) in accordance with the Recommendations (1992) of the International Union of Biochemistry and Molecular Biology (IUBMB)) are enzymes catalysing redox reactions.

According to the invention three types of oxidoreductases are especially contemplated:

a) Laccases or related enzymes cover enzymes which act on molecular oxygen ($O_2$) and yield water ($H_2O$) without any need for peroxide (e.g. $H_2O_2$), b) Oxidases cover enzymes which act on molecular oxygen ($O_2$) and yield peroxide (e.g. $H_2O_2$), and c) Peroxidases cover enzymes which act on peroxide (e.g. $H_2O_2$) and yield water ($H_2O$).

Preferred oxidoreductases are of microbial origin, especially recombinant and/or substantially purified enzymes without any substantial side activity. Microbial enzymes are superior to plant and fruit enzymes as they can be produced more easily in large amounts by recombinant techniques known in the art.

The term "microbial enzyme" in the context of the present invention refers to enzymes derived from bacteria, filamentous fungi or yeasts.

In the case of an enzyme acting on oxygen ($O_2$) as the acceptor, said oxygen may be molecular oxygen supplied by the air. In a preferred embodiment, part of the oxygen is provided by a foam produced from a hair setting/hair dyeing composition comprising a foaming agent.

Suitable enzymatic foam compositions for hair dyeing which may be used according to the invention include hair-dyeing compositions which comprise foaming agent selected from soaps and anionic, cationic, non-ionic, amphoteric, sugar surfactants and/or zwitterionic surfactants and mixtures thereof. The foaming agent(s) may be present at levels of from 0.1% to 15%, preferably from 0.2 to 13%, more preferably from 0.25 to 10%, e.g. from 0.5 to 8% by weight of the final composition. Examples of anionic surfactants suitable for use as the foaming agent are soaps, e.g. in the form of alkali or ethanol amine, isopropanol 2-methyl-2-amino-1,3-propandiol salts of fatty acids such as laurate, myristate, palmitate, stearate, isostearate, behenate, oleate, linoleate, etc.; fatty alcohol ether sulfates such as sodium lauryl ether sulfate; fatty alcohol sulfates such as sodium lauryl sulfate (SLS and SDS); sulfo succinates, e.g. dioctyl sodium sulfo succinate; α-olefin sulfonates; alkyl amide ether sulfates; fatty acid condensation products; alkyl ether phosphates and monoglyceride sulfates. Examples of non-ionic surfactants suitable for use as the foaming agent are especially the nonionic fatty acids and fatty amines that often are used as foam stabilizers, thickeners and boosters, e.g. fatty acid alkanol amides and dialkanol amides and fatty acid alkanol amide polyglycol ethers and fatty amine oxides. Examples of amphoteric surfactants suitable for use in combination with anionic surfactants as the foaming agent are alkyl betaines, alkyl imidazolinium betaines, alkyl sulfo betaines, amidoalkyl betaines, N-alkyl-β-amino propionates, etc.

Examples of foaming agents in the form of sugar surfactants include (a) alkyl- and/or alkenyloligoglycosides and/or (b) fatty acid-N-alkylpolyhydroxyalkylamides. The alkyl- and/or alkenyloligoglycoside (a) has the formula:

R1-O-[G] p         (I), in which R1=4–22 C alkyl and/or alkenyl group, G=a sugar residue with 5 or 6 C and p=1–10. The fatty acid-N-alkylpolyhydroxyalkylamide (b) has the formula:

R2CO—N(R3)-[Z]         (II), in which R2CO=a 6–22 C aliphatic acyl residue, R3=H, alkyl or hydroxyalkyl with 1–4 C and [Z]=a linear or branched polyhydroxyalkyl residue with 3–12 C and 3–10 OH groups;

a) alkyl and alkenyl oligoglycosides of formula R1-O[G]p (I) and b) alkali and/or alkali metal salts of 12–22C secondary 2,3-alkyl sulphates (II). R1=4–22C alkyl and/or alkenyl; G=5–6C sugar residue; p=1–10. The wt. ratio (I):(II) is pref. 1:99–99:1; and (A) fatty acid-N-alkyl polyhydroxyalkyl amides; and (B) sugar surfactants of: (B1) saccharose esters, (B2) sorbitan esters and/or (B3) polysorbates.

A sugar surfactant may also comprise 10–40 (wt.) alkyl and/or alkenyl-oligoglucoside of the formula R1-O-[G]p    (II), 10–40% alkyl- and/or alkenyl-oligoglucoside of the formula R2-O-(G)p    (III), and 80–20% alkyl ether sulphate of the formula R3-(OCH2CH2)nO—SO3M    (IV)

in which R1=8–11C alk(en)yl; (G)=a glucose gp.; p=1–10; (1–3) R2=12–22C alk(en)yl; R3=6–22C alk(en)yl; M=an alkali(ne earth), ammonium or alkanolammonium ion; (pref. Na, Mg) n=1–20 2–7. Pref. R2, R3=12–14C alkyl; and polyglycerine fatty acid ester polyoxyalkylene ether RR1R2R3N+—CH(Y)—CH2-O—CH2-C(CH3)2-C(OH)(H)—C(=O)—NH—CH2CH2-OH X- (I) where R, R1, R2=1–24C alkyl or 8–24C alkenyl; R3=1–18C alkylene; X=monovalent (in)organic anion; and Y=OH or H; and 1–5 wt. % of fatty alcohol polyglycol ether, 1–5% of Guerbet alcohol, 1–5% of polyol partial ester, (B) 1–5% of anionic polymer, (C) 15–30% of fatty alcohol polyglycol ether sulphate, (D) 15–30% of alkyloligoglycoside; and sulphated prods. of fatty acid-N-alkylpolyhydroxyalkyl amides of formula R1CO—N(R2)-Z (I), R1CO=6–22C aliphatic acyl; R2=H, 1–4C alkyl or 1–4C hydroxyalkyl; Z=3–12C polyhydroxyalkyl contg. 3–10 hydroxy gps; and sugar surfactant solubilisers selected from alkyl oligoglycosides of formula (I) and carboxylic acid N-polyhydroxyalkylamides of formula (II). R1-O(G)p (I) R2CO—NR3-Z (II) R1=opt. hydroxylated 1–8C alkyl; G=5C or 6C sugar residue; p=1–10; R2CO=1–8C aliphatic acyl; R3=H, 1–8C alkyl or 1–8C hydroxyalkyl; Z=3–12C polyhydroxyalkyl contg. 3–10 OH gps.

Examples of preferred foaming agents are SDS (sodium dodecyl sulfate), sodium dodecyl ether sulfate and soaps.

It may also be desired to add other additives that function as stabilizers, boosters and thickeners, for example one or more compounds selected from fatty acid alkanol amides, dialkanol amides or fatty alkanol amides, polyglycol ethers such as ethoxylated lauric acid monoethanol amide, or fatty amine oxides such as alkyl dimethyl amine oxide. In connection with an anionic surfactants such as SDS, it will often be preferred to use an amphoteric surfactant such as betaine phosphate.

Also, enzyme systems which comprise a combination of more than one enzyme among the three types of enzymes are contemplated according to the invention. The enzyme systems may e.g. consist of a laccase or a related enzyme and an oxidase; a laccase or a related enzyme and a peroxidase; a laccase or a related enzyme, an oxidase and a peroxidase; or an oxidase and a peroxidase.

Laccases and related enzymes

Laccases (benzenediol:oxygen oxidoreductases) (E.C. class 1.10.3.2 according to Enzyme Nomenclature (1992) Academic Press, Inc) are multi-copper containing enzymes that catalyse the oxidation of phenols. Laccase-mediated oxidations result in the production of aryloxy-radical intermediates from suitable phenolic substrates; the ultimate coupling of the intermediates so produced provides a combination of dimeric, oligomeric, and polymeric reaction products. Certain reaction products can be used to form dyes suitable for dyeing keratinous fibres (see below).

Moreover, the intermediate aryloxy-radical intermediates may themselves possess oxidative properties which may be utilised in e.g. re-formation of disulfide linkages in keratinous fibres of e.g. hair (see below).

Examples of specifically contemplated enzymes within the group of laccases and related enzymes which are capable of oxidising keratin —SH groups and hence re-forming keratin disulfide cross linkages are mono- and diphenolic oxidases, such as catechol oxidase (1.10.3.1), laccase (E.C. 1.10.3.2), tyrosinase (E.C. 1.14.18.1), and bilirubin oxidase (E.C. 1.3.3.5).

Suitable laccases may, for example, be derived from a strain of Polyporus sp., in particular a strain of *Polyporus pinsitus* (also called *Trametes villosa*) or *Polyporus versicolor*, or a strain of Myceliophthora sp., e.g. *M. thermophila* or a strain of Rhizoctonia sp., in particular a strain of *Rhizoctonia praticola* or *Rhizoctonia solani*, or a strain of Scytalidium sp., in particular *S. thermophilium*, or a strain of Pyricularia sp., in particular *Pyricularia oryzae*, or a strain of Coprinus sp., such as a *C. cinereus*.

The laccase may also be derived from a fungus such as Collybia, Fomes, Lentinus, Pleurotus, Aspergillus, Neurospora, Podospora, Phlebia, e.g. *P. radiata* (WO 92/01046), Coriolus sp., e.g. *C. hirsitus* (JP 2-238885), or Botrytis.

In a preferred embodiment of the invention the laccase is derived from a strain of Myceliophthora sp., especially the *Myceliophthora thermophila* laccase described in WO 95/33836 (Novo Nordisk).

When using a laccase, such as the *M. thermophila* laccase, for re-forming keratinous fibre cross links, possibly with simultaneous keratinous fibre dyeing, the invention may be carried out at room temperature, preferably around the optimum temperature of the enzyme, at a pH in the range from 3.0 to 9.0, preferably in the range from 4.0 to 8.0, especially in the range from 6.0 to 8.0.

Bilirubin oxidase may be derived from a strain of Myrothecium sp., such as a strain of *M. verrucaria*.

Peroxidases

Peroxidases are used in combination with either $H_2O_2$ or an oxidase to obtain the desired result, i.e., re-formation of keratin disulfide cross-linkages in e.g. hair.

Suitable peroxidases can be found within the group of enzymes acting on peroxide as acceptor, e.g. E.C. 1.11.1, especially peroxidase (E.C. 1.11.1.7).

Specific examples of suitable enzymes acting on peroxide as acceptor include peroxidases derived from a strain of the fungus Coprinus, in particular a strain of *Coprinus cinereus* or *Coprinus macrorhizus*, or derived from a strain of the bacteria Bacillus, in particular a strain of *Bacillus pumilus*.

Haloperoxidases are also suitable according to the invention. Haloperoxidases form a class of enzymes which are able to oxidise halides ($Cl^-$, $Br^-$, $I^-$) in the presence of hydrogen peroxide to the corresponding hypohalous acids. A suitable haloperoxidase is derivable from Curvularia sp., in particular *C. verruculosa*.

Oxidases

Oxidases yielding peroxide ($H_2O_2$) are used in combination with a peroxidase to remove or at least reduce the peroxide produced.

Suitable oxidases include glucose oxidase (E.C. 1.1.3.4), hexose oxidase (E.C. 1.1.3.5), L-amino-acid oxidase (E.C. 1.4.3.2), xylitol oxidase, galactose oxidase (E.C. 1.1.3.9), pyranose oxidase (E.C. 1.1.3.10) and alcohol oxidase (E.C. 1.1.3.13).

If an L-amino acid oxidase is used, it may be derived from a Trichoderma sp. such as *Trichoderma harzianum*, such as the L-amino acid oxidase described in WO 94/25574 (from Novo Nordisk A/S), or *Trichoderma viride*.

A suitable glucose oxidase may originate from Aspergillus sp., such as a strain of *Aspergillus niger*, or from a strain of Cladosporium sp. in particular *Cladosporium oxysporum*.

Hexose oxidases from the red sea-weed *Chondrus crispus* (commonly known as Irish moss) (Sullivan and Ikawa, (1973), Biochim. Biophys. Acts, 309, p. 11–22; Ikawa, (1982), Meth. in Enzymol. 89, carbohydrate metabolism part D, 145–149) oxidise a broad spectrum of carbohydrates, such as D-glucose, D-galactose, maltose, cellobiose, lactose, D-glucose 6-phosphate, D-mannose, 2-deoxy-D-glucose, 2-deoxy-D-galactose, D-fructose, D-glucuronic acid, and D-xylose.

Also the red sea-weed *Iridophycus flaccidum* produces easily extractable hexose oxidases which oxidise several different mono- and disaccharides (Bean and Hassid, (1956), J. Biol. Chem, 218, p. 425; Rand et al. (1972), J. of Food Science 37, p. 698–710).

Another suitable enzyme group is xylitol oxidase (see e.g. JP 80892242) which oxidises xylitol, D-sorbitol, D-galactitol, D-mannitol and D-arabinitol in the presence of oxygen. A xylitol oxidase can be obtained from strains of Streptomyces sp. (e.g. Streptomyces IKD472, FERM P-14339). Said enzyme has a pH optimum at 7.5 and is stable at pH 5.5 to 10.5 and at temperatures up to 65° C.

In a preferred embodiment of the invention at least one oxidoreductase is used in combination with at least one redox mediator.

A so-called "redox mediator" is sometimes in the literature referred to as "an enhancing agent". In the present context, the term "mediator" will be used.

Thus, in the present context, the term "mediator" is intended to mean an agent capable of enhancing the activity of oxidoreductases.

Although the inclusion of mediators is optional, it is contemplated that in most cases it will be advantageous to include one or more mediators. Without wishing to be limited by any specific theory, it is presently believed that most of the relatively large enzyme molecules will be precluded from the interior of the keratinous fibres of e.g. hair due to their size. Accordingly, in order to take full advantage of the invention the oxidoreductase may conveniently be used in combination with at least one mediator which is readily oxidised by the enzyme and, at the same time, is able to gain access to the interior of the keratinous fibres of e.g. hair, thereby performing the oxidation of keratin —SH groups into keratin disulfide linkages.

The mediator may be a phenolic mediator or a non-phenolic mediator, depending on the particular purpose. Preferably, the mediator should be non-toxic and non-irritating.

Examples of mediators capable of enhancing the activity of oxidoreductases include the compounds described in WO 95/01426, which is hereby incorporated by reference, and represented by the general formula I:

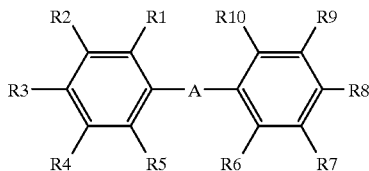

Specifically contemplated compounds within the above formula I include the following: 2,2'-azino-bis(3-ethyl-benzothiazoline-6-sulfonate (ABTS); 6-hydroxy-2-naphtoic acid; 7-methoxy-2-naphtol; 7-amino-2-naphthalene sulfonic acid; 5-amino-2-naphthalene sulfonic acid; 1,5-diaminonaphthalene; 7-hydroxy-1,2-naphthimidazole; 10-methylphenothiazine; 10-phenothiazine-propionic acid (PPT); N-hydroxysuccinimide-10-phenothiazine-propionate; benzidine; 3,3'-dimethylbenzidine; 3,3'-dimethoxybenzidine; 3,3',5,5'-tetramethylbenzidine; 4'-hydroxy-4-biphenylcarboxylic acid; 4-amino-4'-methoxystilbene; 4,4'-diaminostilbene-2,2'-disulfonic acid; 4,4'-diaminodiphenylamine; 2,7-diaminofluorene; 4,4'-dihydroxy-biphenylene; triphenylamine; 10-ethyl-4-phenothiazinecarboxylic acid; 10-ethylphenothiazine; 10-propylphenothiazine; 10-isopropylphenothiazine; methyl-10-phenothiazinepropionate; 10-phenylphenothiazine; 10-allylphenothiazine; 10-phenoxazinepropionic acid (POP); 10-(3-(4-methyl-1-piperazinyl)propyl)phenothiazine; 10-(2pyrrolidinoethyl) phenothiazine; 10-methylphenoxazine; iminostilbene; 2-(p-aminophenyl)-6-methylbenzothiazole-7-sulfonic acid; N-benzylidene-4-biphenylamine; 5-amino-2-naphthalenesulfonic acid; 7-methoxy-2-naphtol; 4,4'-dihydroxybenzophenone; N-(4-(dimethylamino) benzylidene)-p-anisidine; 3-methyl-2-benzothiazolinone(4-(dimethylamino)benzylidene)hydrazone; 2-acethyl-10-methylphenothiazine; 10-(2-hydroxyethyl)phenothiazine; 10-(2-hydroxyethyl)phenoxazine; 10-(3-hydroxypropyl) phenothiazine; 4,4'-dimethoxy-N-methyldiphenylamine, and vanillin azine.

Other mediators contemplated include 4-hydroxybenzoic acid, L-tyrosine, syringate acids, ferulic acid, sinapic acid, chlorogenic acid, caffeic acid and esters thereof.

Still further examples include organic compounds described in WO 96/10079, which is hereby incorporated by reference, and represented by the general formula II:

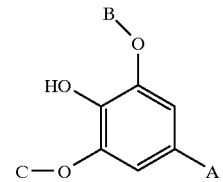

Specific compounds covered by the above formula II are acetosyringone, syringaldehyde, methylsyringate, syringic acid, ethylsyringate, propylsyringate, butylsyringate, hexylsyringate, octylsyringate and ethyl 3-(4-hydroxy-3,5-dimethoxyphenyl)acrylate.

As mentioned above, the present invention also relates to a method for simultaneously re-forming keratinous fibre cross links and dyeing of said keratinous fibres, using at least one precursor.

In the present context the term "precursor" is intended to mean a compound which is converted into a coloured compound (i.e., a dye) by oxidation. Preferably, the precursor is also able to act as a mediator as defined above.

As mentioned above, small aromatic colourless precursors (e.g., p-phenylene-diamine and o-aminophenol) penetrate into the e.g. hair, wool fur, hide or the like where said dye precursors are oxidised by an oxidising agent into coloured polymeric compounds. These coloured compounds are larger than the precursors and cannot be washed out of the e.g. hair.

Without being limited thereto, at least one precursor may be an aromatic compound belonging to one of three major chemical families: the diamines, aminophenols (or aminonaphtols) and the phenols. Examples of isatin derivative precursors can be found in DE 4,314,317-A1.

Furthermore, a number of indole or indoline derivative precursors are disclosed in WO 94/00100, and other suitable benzoic acid precursors are disclosed in WO 98/15257 (Novo Nordisk). Said precursors mentioned in these documents are hereby incorporated herein by reference.

Examples of such suitable precursors include compounds from the group comprising p-phenylene-diamine (pPD), p-to-luylene-diamine, chloro-p-phenylenediamine, p-aminophenol, o-aminophenol and 3,4-diaminotoluene, 2-methyl-1,4-diaminobenzene, 4-methyl-o-phenylenediamine, 2-methoxy-p-phenylenediamine, 2-chloro-1,4-diamino-benzene, 4-amino diphenylamine, 1-amino-4-β-methoxyethylamino-benzene, 1-amino-4-bis-(β-hydroxyethyl)-aminobenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-benzene, 1-hydroxy-4-methylamino-benzene, 1-methoxy-2,4-diamino-benzene, 1-ethoxy-2,3-diamino-benzene, 1-β-hydroxyethyloxy-2,4-diamino-benzene, phenazines, such as 4,7-phenazinedicarboxylic acid, 2,7-phenazinedicarboxylic acid, 2-phenazinecarboxylic acid, 2,7-diaminophenazine, 2,8-diaminophenazine, 2,7-diamino-3,8-dimethoxyphenazine, 2,7-diamino-3-methoxyphenazine, 2,7-diamino 3-methoxyphenazine, 3-dimethyl 2,8-phenazinediamine, 2,2'-[(8-amino-7-methyl-2-phenazinyl)imino]bis-ethanol, 2,2'-[(8-amino-7-methoxy-2-phenazinyl)imino]bis-ethanol, 2,2'-[(8-amino-7-chloro-2-phenazinyl)imino]bis-ethanol, 2-[(8-amino-7-methyl-2-phenazinyl)amino]-ethanol, 2,2'-[(8-amino-2-phenazinyl)imino]bis-ethanol, 3-amino-7-(dimethylamino)-2,8-dimethyl-5-phenyl-chloride, 9-(diethylamino)benzo[a]phenazine-1,5-diol, N-[8-(diethylamino)-2-phenazinyl]-methanesulfonamide, N-(8-methoxy-2-phenazinyl)methanesulfonamide, N,N,N',N'-tetramethyl-2,7-phenazinediamine, 3,7-dimethyl-2-phenazinamine, p-amino benzoic acids, such as p-amino benzoic acid ethyl, p-amino benzoic acid glycerid, p-amino benzoic acid isobutyl, p-dimethylamino benzoic acid amil, p-dimethylamino benzoic acid octyl, p-diethoxy amino benzoic amil, p-dipropoxy amino benzoic acid ethyl, acetylsalicylic acid, and isatin derivatives, such as 2,3-diamino benzoic acid, and mixtures of the above precursors.

Specifically contemplated mixtures of precursors include the mixtures published in DK patent appln. no. 358/98 (see especially table in FIGS. 1 to 3).

In one embodiment of the invention, the laccase or other oxidoreductase is used in combination with the precursor (but without a separate mediator) to oxidise the precursor into a coloured compound and at the same time re-form disulfide linkages in the keratinous fibres of e.g. hair. In this case, the precursor also functions as a mediator. The precursor may be used in the form of a single precursor or as a combination of two or more precursors.

If, however, the precursor is not able to act as a mediator, i.e., mediate the re-formation of disulfide linkages in the e.g. hair, the laccase or other oxidoreductase and the precursor will be used with at least one mediator as defined above.

By including compounds referred to as modifiers (also known as couplers) in the dyeing composition a number of colour tints can be obtained. Cathecol and Resorcinol are examples of such modifiers.

Preferably, at least one modifier is used in combination with the oxidoreductase in the method of the invention, thereby allowing a number of colour tints to be obtained. In general, modifiers are used in dyeing methods, as the colours resulting from hair dyeing without a modifier are usually unacceptable for most people.

Modifiers are typically m-diamines, m-aminophenols, or polyphenols or a combination thereof. The modifier reacts with the precursor in the presence of the oxidative enzyme, converting it into a coloured compound.

Examples of modifiers include m-phenylene-diamine, 2,4-diaminoanisole, 1-hydroxynaphthalene(α-naphthol), 1,4-dihydroxybenzene(hydroquinone), 1,5-dihydroxynapthalene, 1,2-dihydroxybenzene(pyrocatechol), 1,3-dihydroxybenzene (resorcinol), 1,3-dihydroxy-2-methylbenzene, 1,3-dihydroxy-4-chlorobenzene(4-chlororesorcinol), 1,2,3,trihydroxybenzene, 1,2,4-trihydroxybenzene, 1,2,4-trihydroxy-5-methylbenzene and 1,2,4-trihydroxytoluene, and mixtures thereof.

In a preferred embodiment of the invention, the oxidoreductase and the precursor are used in combination with at least one modifier as defined above.

In conclusion, the use of oxidoreductases such as laccases is an improvement over the more traditional use of $H_2O_2$ in hair setting methods, as peroxide can damage the keratinous fibres. In contrast hereto, the reaction with the oxygen needed for laccase-mediated oxidation comes from the air, rather than via harsh chemical oxidation.

Finally the invention relates to a composition suitable for setting of keratinous fibres, such as hair, comprising at least one oxidoreductase and further ingredients used in setting compositions. The oxidoreductase may be any of the above mentioned.

The term "ingredients used in setting compositions" means ingredients know by the skilled person with skill in the field of formulating of hair care composition to be incorporated in prior art compositions.

MATERIALS AND METHODS

Materials

*Myceliophthora thermophila* laccase described in WO 95/33836 (Novo Nordisk)

Methods

Determination of *M. thermophila* laccase activity (LAMU)

Manual method

PRINCIPLE

Laccase (E.C. 1.10.3.2), p-diphenol:$O_2$ oxidoreductase, containing copper in the prosthetic group, uses molecular oxygen as a final electron acceptor. Atmospheric oxygen is directly reduced to 2 $H_2O$, during liberation of 4 electrons, without hydrogen peroxide being an intermediate step.

Laccase will under aerobic conditions catalyze the oxidation of syringaldazin forming tetra metoxy-azo bis methylene quinone.

Reaction conditions

Substrate: Syringaldazin 19 microM

Buffer: Tris 23 mM pH: 7.50

Temperature: 30° C.

Time of reaction: 90 sec.

Enzyme working area: 0.0016–0.0064 LAMU/mL

Wavelength: 530 nm

Water: MilliQ

Definition of units

One LAMU, is the amount of enzyme which under the given analytical conditions transforms 1 micro mole syringaldazin per minute.

SPECIFICITY AND SENSITIVITY

Limit of detection LOD: 0.007 LAMU/mL

Limit of quantification LOQ: 0.07 LAMU/mL

Range: 0.100–0.400 ABS/min.
REAGENTS/SUBSTRATES
Maleic acid, 1.0M

Maleic acid 37% paM *) 800380 23.2 g

Demineralized water, MilliQ up to 200 mL 23.2 g Maleic Acid is weighed in a weighing boat and added 150 mL water during continuously stirring. Stir until dissolved.

Transfer quantitatively the solution to a 200 mL volumetric flask and add up to the mark with water.

*) pro analysi Merck
Tris buffer 1.0M; Stock solution

Tris[hydroxymethyl]aminomethane Sigma T-1378 121.1 g

Demineralized water, MilliQ up to 1 L

Tris buffer is weighed in a weighing boat and 800 mL of water is added during continuously stirring. Stir until dissolved.

Transfer quantitatively the solution to a 1 L volumetric flask and add up to the mark with water.
Tris buffer 25 mM; pH 7.50

Tris buffer 1.0M . . . 25.0 mL

Maleic acid , 1.0M . . . 5.0 mL

Demineralized water . . . up to 1 L pH is adjusted to 7.50±0.05.

Pour 50 mL Tris buffer 1.0M (graduated glass) into a 1 L volumetric flask and add about 700 mL water. Now add 5 mL Maleic acid, 1M. Adjust pH to 7.50±0.05 and add up to the mark with water. (pH may not be adjusted with HCl, because of the inhibiting effect on the Laccase-enzyme.)
Dilution media PEG 6000 paM 807491 25.0 g Triton X-100, Sigma T-9284 5.0 g MilliQ water up to 0.5 L 25.0 g PEG 6000 and 5.0 g Triton X-100 is weighed in a weighing boat and added 400 mL water during continuous stirring. Stir until dissolved.

Transfer quantitatively the solution to a 0.5 L volumetric flask and add up to the mark with water.
Syringaldazin, 0.56 mM; Stock solution Syringaldazin anh Sigma S-7896 10.0 mg Ethanol96% . . . 50 mL Syringaldazin is weighed in a 50 mL volumetric flask and added ethanol of 50 mL. Is stirred until dissolved (ap. 3 hours). The reagent is sensitive to light. Should be contained in a dark bottle.
Syringaldazin, 0.28 mM; 48% ethanol Syringaldazin, 0.56 mM 25.0 mL Demineralized water, MilliQ up to 50 mL 25 mL syringaldazin, 0.56 mM (full pipette) is transferred to a 50 mL volumetric flask. Fill up to the mark with water.
Check of the Reagent: Syringaldazin, 0.056 mM; 48% ethanol Syringaldazin, 0.28 mM 2 mL Ethanol, 96% 4 mL Demineralized water, MilliQ up to 10 mL The solution should have an absorption of about 2.2 at 360 nm. measured against ethanol, 6%.
Ethanol, 6%

Ethanol, 96% 62.5 mL

Demineralized water, Milli Q up to 1000 L 62.5 mL ethanol, 96% (graduated glass) is transferred to a 1 L volumetric flask. Fill up to the mark with water.

SAMPLES AND STANDARDS
Control

The analyses are compared to a well known laccase sample in order to control the level of the assay. The sample is a representative laccase batch.
Unknown samples The Laccase samples are diluted to an expected activity of 0.18 LAMU/mL with the dilution media. Let the samples rest for 15 minutes before analysis.

Working area: 0.07–0.28 LAMU/mL.

Other samples with precipitate are centrifuged at about 3000 rpm. for 10 minutes.
PROCEDURE Reagents and standards are made. The samples are weighed and diluted to an expected activity at 0.18 LAMU/mL.

4 mL Tris buffer, 25 mM; pH 7.5 is preheated in at least 10 minutes at 30° C. A 100 microL sample is added. Mixing. 300 microL syringaldazin, 0.28 mM is added whereby the reaction is started. Mixing.

The sample is mounted into the photometer, on which afterwards the kin-e-tic sequence at 530 nm is read, and a change in absorption is calculated per minute from $t_{90sec.} - t_{60sec.}$. See table 1 below. Between each sample the photometer cuvette is rinsed with a 6% ethanol solution.

TABLE 1

| Procedure for laccase | |
|---|---|
| Tris buffer 25 mM; pH 7.5 (reagent 6.3) Heating, 10 minutes, 30° C. | 4.00 mL |
| Enzyme Mixing | 100 µl |
| Syringaldazin 0.28 mM (reagent 6.6) Mixing | 300 µl |
| Reading t = 90 seconds at 530 nm Calculation: $t_{90\ seconds} - t_{60\ seconds}$ Rinse with 6% ethanol | |

CALCULATION $$\frac{\Delta ABS \times 4.4 \times 10^{-3}}{0.065 \times 0.1} \times D = LAMU\,/\,mL$$

Where:

Δ ABS: change in absorption per minute.

4.4: total volume in mL.

0.1: assay volume in mL.

0.065: micro molar extinction coefficient.

$10^{-3}$: LAMU/L→LAMU/mL.

D: Further dilution.

EXAMPLES

Example 1

Natural brown hair (De Meo Brothers, 8 inches, approximately one gram) was set in the desired physical conformation (curled), then treated with a conventional waving lotion (Rave moisture lock home perm 3, approximately 15 mL) to reduce disulfide bonds. The hair was briefly submerged in the reducing solution, then removed. Excess solution was wiped off, and the hair was left standing for 20 minutes. Hair was rinsed thoroughly with water, then subjected to the second stage of the treatment, which combined dyeing of hair with re-formation of cross links (to complete the setting treatment). Hair samples were submerged in 10 mL of a precursor solution (0.05M NaOAc buffer, pH 6.5, 0.1% w/w para-phenylenediamine, 0.07% w/w meta-phenylenediamine), to which was added *Myceliophthora thermophila* laccase (50 μL of a 1170 LAMU/mL solution). The hair was agitated briefly in solution, then removed from solution and allowed to stand for 25 minutes, at which point the hair was thoroughly rinsed with water.

We claim:

1. A method for re-forming keratinous fibre cross links comprising 1) reducing covalent disulfide linkages in the keratinous fibres and 2) contacting the reduced keratinous fibres with at least one oxidoreductase for a sufficient period of time and under conditions sufficient to permit re-formation of the keratinous fibre cross links.

2. A method according to claim 1, comprising contacting the oxidoreductase in combination with at least one mediator with the keratinous fibres for a sufficient period of time and under conditions sufficient to permit re-formation of keratinous fibre cross links.

3. A method according to claim 1, wherein the oxidoreductase is derived from a microorganism.

4. A method according to claim 1, wherein the oxidoreductase is a laccase, an oxidase, a peroxidase, or a mixture thereof.

5. A method according to claim 4, wherein the oxidoreductase is a laccase derived from Myceliophthora sp.

6. A method according to claim 2, wherein the mediator is selected from the group consisting of 2,2'-azino-bis(3-ethylbenzothiazoline-6-sulfonate (ABTS), 6-hydroxy-2-naphtoic acid, 7-methoxy-2-naphtol, 7-amino-2-naphthalene sulfonic acid, 5-amino-2-naphthalene sulfonic acid, 1,5-diaminonaphthalene, 7-hydroxy-1,2-naphthimidazole, 10-methylphenothiazine, 10-phenothiazine-propionic acid (PPT), N-hydroxysuccinimide-10-phenothiazine-propionate, benzidine, 3,3'-dimethylbenzidine, 3,3'-dimethoxybenzidine, 3,3',5,5'-tetramethylbenzidine, 4'-hydroxy-4-biphenylcarboxylic acid, 4-amino-4'-methoxystilbene, 4,4'-diaminostilbene-2,2'-disulfonic acid, 4,4'-diaminodiphenylamine, 2,7-diaminofluorene, 4,4'-dihydroxy-biphenylene, triphenylamine, 10-ethyl-4-phenothiazinecarboxylic acid, 10-ethylphenothiazine, 10-propylphenothiazine, 10-isopropylphenothiazine, methyl-10-phenothiazinepropionate, 10-phenylphenothiazine, 10-allylphenothiazine, 10-phenoxazinepropionic acid (POP), 10-(3-(4-methyl-1-piperazinyl)propyl)phenothiazine, 10-(2-pyrrolidinoethyl)phenothiazine, 10-methylphenoxazine, iminostilbene, 2-(p-aminophenyl)-6-methylbenzothiazole-7-sulfonic acid, N-benzylidene-4-biphenylamine, 5-amino-2-naphthalenesulfonic acid, 7-methoxy-2-naphtol, 4,4'-dihydroxybenzophenone, N-(4-(dimethylamino)benzylidene)p-anisidine, 3-methyl-2-benzothiazolinone(4-(dimethylamino)benzylidene)hydrazone, 2-acethyl-10-methylphenothiazine, 10-(2-hydroxyethyl)phenothiazine, 10-(2-hydroxyethyl)phenoxazine, 10-(3-hydroxypropyl)phenothiazine, 4,4'-dimethoxy-N-methyldiphenylamine, vanillin azine, 4-hydroxybenzoic acid, L-tyrosine, syringate acids, ferulic acid, sinapic acid, chlorogenic acid, caffeic acid and esters thereof, acetosyringone, syringaldehyde, methylsyringate, syringic acid, ethylsyringate, propylsyringate, butylsyringate, hexylsyringate, octylsyringate and ethyl 3-(4-hydroxy-3,5-dimethoxyphenyl)acrylate, and combinations thereof.

7. A method according to claim 2, comprising contacting keratinous fibres with at least one oxidoreductase and at least one mediator in combination with at least one precursor to obtain dyeing by oxidation of the precursor into a coloured compound.

8. A method according to claim 7, wherein the precursor is selected from the group consisting of diamines, aminophenols, aminonaphtols, phenols, and mixtures thereof.

9. The method according to claim 3, wherein the oxidoreductase is derived from bacteria, filamentous fungi or yeasts.

10. The method according to claim 5, wherein the laccase is derived from *M. thermophila*.

11. A method for re-forming keratinous fibre cross links and simultaneously dyeing such keratinous fibres comprising 1) reducing covalent disulfide linkages in the keratinous fibres and 2) contacting the reduced keratinous fibres with at least one oxidoreductase and at least one precursor for a sufficient period of time and under conditions sufficient to permit oxidation of the precursor into a coloured compound and to permit re-formation of the keratinous fibre cross links.

12. A method according to claim 11, comprising contacting the oxidoreductase and the precursor in combination with at least one modifier with the keratinous fibres for a sufficient period of time and under conditions sufficient to permit oxidation of the precursor into a coloured compound and to permit re-formation of keratinous fibres cross links.

13. The method according to claim 11, wherein the oxidoreductase is of microbial origin.

14. A method according to claims 11, wherein the precursor is selected from the group consisting of diamines, aminophenols, aminonaphtols, phenols, and mixtures thereof.

15. A method according to claim 12, wherein the modifier is selected from the group consisting of m-diamines, m-aminophenols, and polyphenols, and mixtures thereof.

16. The method according to claim 13, wherein the oxidoreductase is of bacterial, filamentous fungus or yeast origin.

17. The method according to claim 16, wherein the oxidoreductase is a laccase, an oxidase, a peroxidase, or a mixture thereof.

18. The method according to claim 17, wherein the laccase is derived from Myceliophthora sp.

19. The method according to claim 18, wherein the laccase is derived from *M. thermophila*.

* * * * *